United States Patent
Kim et al.

(10) Patent No.: US 6,365,697 B1
(45) Date of Patent: *Apr. 2, 2002

(54) WATER-SOLUBLE OR WATER-DISPERSIBLE POLYURETHANES WITH TERMINAL ACID GROUPS, THE PRODUCTION AND THE USE THEREOF

(75) Inventors: Son Nguyen Kim, Hemsbach; Karin Sperling, Neustadt, both of (DE)

(73) Assignee: BASF Aktiengesellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/068,009

(22) PCT Filed: Nov. 6, 1995

(86) PCT No.: PCT/EP96/04858

§ 371 Date: Apr. 29, 1998

§ 102(e) Date: Apr. 29, 1998

(87) PCT Pub. No.: WO97/17386

PCT Pub. Date: May 15, 1997

(30) Foreign Application Priority Data

Nov. 6, 1995 (DE) .......................................... 195 41 326

(51) Int. Cl.[7] ........................ C08G 18/32; C08G 18/40; C08G 18/38; C08J 3/03; A61K 7/06
(52) U.S. Cl. ..................... 528/28; 424/70.1; 424/70.11; 424/70.12; 424/70.122; 424/70.17; 424/78.08; 424/78.37; 524/591; 524/840; 528/49; 528/59; 528/60; 528/61; 528/71; 528/80; 528/83
(58) Field of Search ................................ 524/591, 840; 528/60, 61, 71, 80, 83, 49, 59, 28; 424/70.1, 70.11, 70.12, 70.122, 70.17, 78.08, 78.37

(56) References Cited

U.S. PATENT DOCUMENTS

| | | | |
|---|---|---|---|
| 3,412,054 A | 11/1968 | Milligan et al. | ............. 524/591 |
| 3,475,206 A | 10/1969 | Heyden | ...................... 117/142 |
| 3,523,998 A | 8/1970 | Feinstone et al. | .............. 424/78 |
| 3,658,939 A | 4/1972 | Carpenter et al. | ............. 528/83 |
| 3,734,874 A | 5/1973 | Kobler et al. | ................ 524/603 |
| 3,836,537 A | 9/1974 | Boerwinkle et al. | ......... 524/548 |
| 3,943,252 A | 3/1976 | Schroer et al. | .............. 428/262 |
| 3,948,837 A * | 4/1976 | Schmitt et al. | .............. 524/839 |
| 4,108,814 A * | 8/1978 | Reiff et al. | .................. 524/840 |
| 4,150,216 A | 4/1979 | Quack et al. | ................ 528/290 |
| 4,179,420 A | 12/1979 | Laganis et al. | .............. 524/598 |
| 4,182,828 A * | 1/1980 | Reischl et al. | ......... 442/59 |
| 4,237,253 A | 12/1980 | Jacquet et al. | ................ 526/75 |
| 4,248,745 A | 2/1981 | Laganis | ...................... 528/272 |
| 4,300,580 A | 11/1981 | O'Neill et al. | .................. 132/7 |
| 4,324,780 A | 4/1982 | Jacquet et al. | ................ 424/47 |
| 4,743,673 A | 5/1988 | Johnston et al. | .............. 528/60 |
| 4,804,719 A | 2/1989 | Weaver et al. | .............. 525/420 |
| 4,814,101 A | 3/1989 | Shieferstein et al. | ........ 252/174 |
| 5,626,840 A | 5/1997 | Thomaides et al. | ........... 424/70 |
| 6,277,386 B1 * | 8/2001 | Kim et al. | ................... 424/401 |

FOREIGN PATENT DOCUMENTS

| | | |
|---|---|---|
| CA | 2066226 | 3/1991 |
| CA | 2148805 | 6/1994 |
| CA | 2128949 | 1/1995 |
| CA | 2132905 | 4/1995 |
| CA | 2175531 | 11/1996 |
| CA | 2189886 | 5/1997 |
| DE | 3929973 | 9/1989 |
| DE | 4225045 | 7/1992 |
| DE | 4311039 | 10/1992 |
| DE | 4241118 | 12/1992 |
| GB | 1128568 | 9/1968 |
| GB | 1329565 | 9/1973 |
| GB | 1368495 | 9/1974 |
| JP | 5295078 | 11/1993 |
| WO | 9508583 | 9/1993 |
| WO | 95/08583 * | 3/1995 |

* cited by examiner

Primary Examiner—Rabon Sergent
(74) Attorney, Agent, or Firm—Keil & Weinkauf

(57) ABSTRACT

The present invention relates to water-soluble or water-dispersible polyurethanes of a water-dispersible polyurethane prepolymer having terminal isocyanate groups and a primary or secondary amine having at least one ionogenic or ionic group, and to the salts thereof. The novel polyurethanes can be used as auxiliaries in cosmetology and pharmacy and, in particular, as hair lacquers having enhanced ease of washoff.

23 Claims, No Drawings

WATER-SOLUBLE OR WATER-DISPERSIBLE POLYURETHANES WITH TERMINAL ACID GROUPS, THE PRODUCTION AND THE USE THEREOF

The present present invention relates to water-soluble or water-dispersible polyurethanes with terminal acid groups, to their preparation and to their use in cosmetology.

Water-soluble or water-dispersible polymers, for example polyesters, polyamides or polyurethanes, are becoming increasingly important on the basis of their particularly low viscosity in water/ethanol. For instance, water-soluble polyurethanes comprising carboxyl-containing diols in copolymerized form are disclosed in U.S. Pat. Nos. 3,412,054 and 3,658,939. They are used as adhesives, as coating compositions and in printing inks. Water-dispersible polyurethanes containing sulfonate groups and/or carboxylate groups are disclosed in DE-A-15 70 615. They are used, for example, for coating and for the impregnation of textiles, leather, paper, wood and metals. Patent documents U.S. Pat. No. 4,300,580, U.S. Pat. No. 3,734,874, DE-A-26 33 418 and WO-A-89/07118 disclose polyesters which contain $NaSO_3$ groups and whose main chain is synthesized by condensation reaction and can be broken into shorter segments by hydrolyzing the ester groups.

It is also known that maleic anhydride and trimellitic anhydride can be used to prepare water-soluble esters. The anhydride group provides carboxyl groups which, by neutralization with amines, metal hydroxides and metal carbonates, are converted to water-solubilizing carboxylate groups. DE-A-26 37 167 and U.S. Pat. No. 3,523,998 disclose that polycarboxylic acids and their anhydrides can, as polymer components, also contribute to rendering polyesters soluble in water. DE-A-21 44 878 describes polyurethanes which are reaction products of digested casein, water-dispersible polyurethanes and formaldehyde. The polyurethane component employed is, inter alia, a latex obtainable by reacting a polyurethane prepolymer with a sodium taurine solution. The latex has a relatively low molecular weight and a low content of ionogenic or ionic groups, since other than the sulfonate groups from the taurine it contains no further ionogenic or ionic groups. A film obtained from the latex, therefore, is insoluble in water without dispersants. The resulting latex is then reacted with casein and formaldehyde to give the abovementioned reaction product. However, no cosmetic application of such polymers has yet been described.

Film-forming polymers are used in cosmetology to improve the structure of and to shape and set the hair. The hair treatment compositions generally comprise a solution of the film former in an alcohol or in a mixture of alcohol and water.

U.S. Pat. No. 4,743,673 describes hydrophilic polyurethane polymers with carboxyl groups in the polymer backbone. These polyurethanes are synthesized from a polyol component, which can be an alkylene glycol, a polyoxyalkylene glycol or a linear polyesterdiol, from a carboxylic ester component containing hydroxyl or amino groups, and from an organic isocyanate or isocyanate precursor. The polyurethane therefore contains ester groups attached to the polymer backbone, which are subsequently hydrolyzed by heating under reflux for 30–60 minutes with a strong base, such as sodium hydroxide or potassium hydroxide. The product no longer gives a clear solution either in water or in ethanol. Especially when using a polyesterdiol as polyol component, treatment with the strong base under reflux conditions gives rise to hydrolysis not only of the ester groups of the carboxylic ester component but also of those present in the polyurethane chain. The latter is thus cleaved, with a drastic reduction in the molecular weight of the polyurethanes. Admittedly, use of polyurethanes in hairsprays is mentioned; however, the films obtained with these polyurethanes cannot in practice be used for hair cosmetology since they are either insoluble in water or have an inadequate molecular weight and therefore an insufficient setting effect.

DE-A-42 25 045 describes the use of water-soluble or water-dispersible anionic polyurethanes as hair lacquers. These polyurethanes are composed of
 a) at least one compound containing two or more active hydrogen atoms per molecule,
 b) at least one diol containing acid groups or salt groups, and
 c) at least one diisocyanate.

They have a glass transition temperature of at least 15° C. and an acid number of 12–150. Preferred components a) employed are polyethylene glycol, neopentylglycol and polyesterols. Preferred components b) are dimethylolpropanoic acid, a condensation product of pyromellitic dianhydride and neopentylglycol, and a condensation product of 5-sodium-sulfonatoisophthalic acid with neopentylglycol.

DE-A-42 41 118 describes the use of cationic polyurethanes and polyureas as auxiliaries in cosmetic and pharmaceutical formulations. They are employed in particular as a film former in hair lacquers, and are composed of
 a) at least one diisocyanate which can have already been reacted beforehand with one or more compounds containing two or more active hydrogen atoms per molecule, and
 b) at least one diol, primary or secondary amino alcohol, primary or secondary diamine or primary or secondary triamine having one or more tertiary, quaternary or protonated tertiary amine nitrogen atoms.

The polymers have a glass transition temperature of at least 25° C. and an amine number of 50–200, based on the nonquaternized or protonated compounds.

EP-A-619 111 describes the use of polyurethanes containing carboxylate groups in hairsetting compositions. To provide the carboxylate groups the polyurethanes comprise a compound of the formula

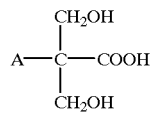

in which A is hydrogen or $C_1$–$C_{20}$-alkyl. At least some of the carboxylic acid groups are then neutralized with an organic or inorganic base in order to provide the number of carboxylate groups required to render the polyurethane soluble in water or in a mixture of water and a polar organic solvent.

Hairsetting compositions are generally applied to the hair by spraying in the form of aqueous-alcoholic solutions. After solvent evaporation, the hair is held in the desired shape at the points of mutual contact of the residual polymer. The polymers should be sufficiently hydrophilic to enable washoff from the hair but sufficiently hydrophobic for the polymer-treated hair to retain its shape, even in the case of high atmospheric humidity, and for the individual hairs not to stick to one another. For a maximum hairsetting effect it is additionally desirable to employ polymers with a relatively high molecular weight (K value>25) and a relatively high glass transition temperature (at least 15° C.). However, the higher molecular weight of polymers meeting these requirements reduces the ease of washoff.

When formulating hair lacquers, another factor to consider is that a reduction in the content of alcohol and of propellent is necessary owing to environmental regulations regarding the control of the emission of volatile organic compounds (VOCs) into the atmosphere.

The polymers described in the abovementioned publications go only part way to meeting these contradictory requirements. For instance, although the high molecular weight of the polymers described in DE-A-42 25 045 and 42 41 118 and in EP-A-619 111 give them the desired setting effect, they are not sufficiently easy to wash off. The polymers described in U.S. Pat. No. 4,743,673, in turn, because of the low molecular weight which they have as a result of hydrolysis of the ester groups, do not possess the required setting effect.

EP-A-636 361 describes cosmetic compositions which include as a film former a polycondensation product comprising at least one polysiloxane unit and at least one polyurethane unit and/or polyurea unit having anionic or cationic groups. The ease of washoff of these film formers is also not satisfactory.

It is therefore the object of the present invention to provide hair treatment compositions which can be used as hair lacquers but which also have improve ease of washoff (redispersibility).

We have found that this object can be achieved, surprisingly, by means of water-soluble or water-dispersible polyurethanes which are the reaction product of a urethane prepolymer having terminal isocyanate groups with a primary or secondary amine which has at least one ionogenic or ionic group.

The present invention therefore provides water-soluble or water-dispersible polyurethanes of A) a water-soluble or -dispersible polyurethane prepolymer having terminal isocyanate groups, and B) at least one primary or secondary amine which has at least one ionogenic or ionic group, and the salts thereof.

The primary or secondary amine reacts with the terminal isocyanate groups of the urethane prepolymer so that the amine is attached to the polyurethane via a urea group. Therefore, the novel polyurethanes contain terminal groups which are derived from the amine and each have at least one ionogenic or ionic group. They preferably have a K value of 15–100, in particular 20–50, and a glass transition temperature $T_g$ of 15–150, in particular 25–100.

If the polyurethanes comprise carboxyl or sulfo groups, the acid number is preferably 12–150, in particular 30–90.

If the polyurethanes comprise amine groups and/or protonated or quaternized amine groups, the amine number is preferably 30–180, in particular 50–120.

Polyurethane prepolymers which can be used in accordance with the invention are known. These are polyurethanes which have ionogenic or ionic groups attached to the polymer chain, thereby rendering the polyurethanes dispersible or soluble in water. These groups are preferably carboxyl groups and/or sulfo groups and/or nitrogen-containing groups (amines) or carboxylate groups and/or sulfonate groups and/or quaternized or protonated groups. Such polyurethane prepolymers are formed from:

a) at least one compound containing two or more active hydrogen atoms per molecule, b) at least one compound containing two or more active hydrogen atoms and at least one ionogenic or ionic group per molecule, and c) at least one diisocyanate.

Component (a) especially comprises diols, diamines, amino alcohols, polyetherdiols and polyesterdiols having a number-average molecular weight of in each case up to 3,000, or mixtures thereof, it being possible for up to 3 mol-% of said compounds to be replaced by triols or triamines. A particularly preferred component (a) employed is a diol mixture comprising at least 30% by weight, in particular 40–80% by weight, based on the overall weight of components (a) and (b), of a polyesterdiol.

Examples of diols which can be used are ethylene glycol, propylene glycol, butylene glycol, neopentylglycol, polyetherols, such as polyethylene glycols having molecular weights of up to 3,000, block copolymers of ethylene oxide and propylene oxide having number-average molecular weights of up to 3,000, or block copolymers of ethylene oxide, propylene oxide and butylene oxide in which the copolymerized alkylene oxide units are present, in random distribution or in the form of blocks. Preference is given to ethylene glycol, neopentylglycol, and di-, tri-, tetra-, penta- or hexaethylene glycol.

Examples of suitable amino alcohols are 2-aminoethanol, 2-(N-methylamino)ethanol, 3-aminopropanol and 4-aminobutanol.

Examples of suitable diamines are ethylenediamine, propylenediamine, 1,4-diaminobutane and 1,6-diaminohexane, and also α,ω-diamines which can be prepared by aminating polyalkylene oxides with ammonia.

Suitable polyesterdiols are all those customarily employed for preparing polyurethanes, especially those based on aromatic dicarboxylic acids, such as terephthalic acid, isophthalic acid, phthalic acid, Na- or K-sulfoisophthalic acid, etc., aliphatic dicarboxylic acids, such as adipic acid or succinic acid, etc., and cycloaliphatic dicarboxylic acids, such as 1,2-, 1,3- or 1,4-cyclohexanedicarboxylic acid. Suitable diols are, especially, aliphatic diols, such as ethylene glycol, propylene glycol, 1,6-hexanediol, neopentyl glycol, diethylene glycol, polyethylene glycols, polypropylene glycols, 1,4-dimethylolcyclohexane, and also poly(meth)acrylatediols of the formula

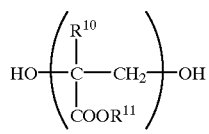

in which $R^{10}$ is H or $CH_3$ and $R^{11}$ is $C_1$–$C_{18}$-alkyl (especially $C_1$–$C_{12}$- or $C_1$–$C_8$-alkyl) which have a molar mass of up to about 3000. Diols of this kind can be prepared in a conventional manner and are obtainable commercially (Tegomer® grades MD, BD and OD from Goldschmidt).

Preference is given to polyesterdiols based on aromatic and aliphatic dicarboxylic acids and on aliphatic diols, especially those for which the aromatic dicarboxylic acid makes up from 10 to 95 mol-%, in particular from 50 to 90 mol-% and, preferably from 70 to 85 mol-%, of the overall amount of dicarboxylic acid (the remainder being aliphatic dicarboxylic acids).

Particularly preferred polyesterdiols are the reaction products of phthalic acid/diethylene glycol, isophthalic acid/1,4-butane-diol, isophthalic acid/adipic acid/1,6-hexanediol, 5-$NaSO_3$-isophthalic acid/phthalic acid/adipic acid/1,6-hexanediol, adipic acid/ethylene glycol, isophthalic acid/adipic acid/neopentyl glycol, isophthalic acid/adipic acid/neopentyl glycol/diethylene glycol/dimethylolhexane and 5-$NaSO_3$-isophthalic acid/isophthalic acid/adipic acid/neopentyl glycol/diethylene glycol/dimethylolcyclohexane.

The polyesterdiols preferably have a molar mass in the range from about 400 to 5000, in particular from 500 to 3000.

Polyurethanes based on these polyesterdiols and on aliphatic diisocyanates are of particular advantage because they are biodegradable.

As component (a) it is also possible to use silicone compounds of the formula

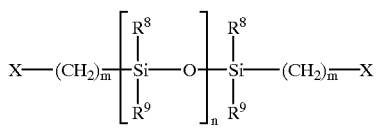

where $R^8$ and $R^9$ can be identical or different and are $C_1$–$C_4$-alkyl, benzyl or phenyl, preferably methyl, the radicals X can be identical or different and are OH or $NH_2$, m is 2–8, and n is 5–50, especially 3–30.

These silicone compounds can be employed in a quantity of up to 50% by weight, in particular up to 30% by weight, based on the overall weight of components (a) and (b).

The polysiloxane-containing polyurethanes act as solubilizers for hydrophobic products, especially silicones, and therefore permit them to be included in the hair treatment compositions. The silicones make the hair shiny, soft and smooth and are preferably present in amounts of up to 0.2% by weight, based on the overall weight of the composition. It is preferred to use nonvolatile silicones, especially those based on poly(dimethylsiloxane).

Particularly suitable silicones are dimethicones, examples being the Abil® grades from Goldschmidt.

If compounds with carboxylate groups or sulfonate groups are employed as component (b), anionic polyurethanes are obtained. A particularly preferred component (b) is dimethylolpropanoic acid. Other compounds which can be used are those of the formulae

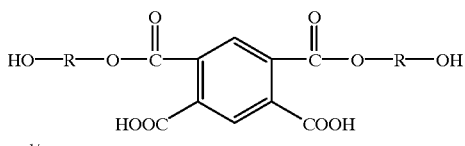

and/or

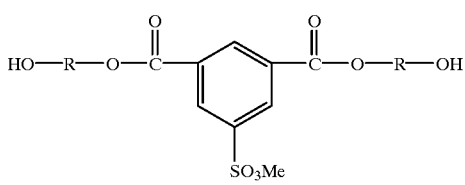

where each R is $C_2$–$C_{18}$-alkylene and Me is Na or K.

Other compounds which can be used as component (b) are those of the formula

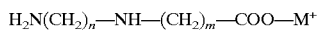

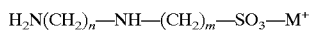

where m and n independently of one another are an integer from 1 to 8, especially 1 to 6, and M is Li, Na or K.

If compounds with nitrogen-containing groups are used as component (b), cationic polyurethanes are obtained.

Examples of components (b) which can be used are compounds of the general formulae

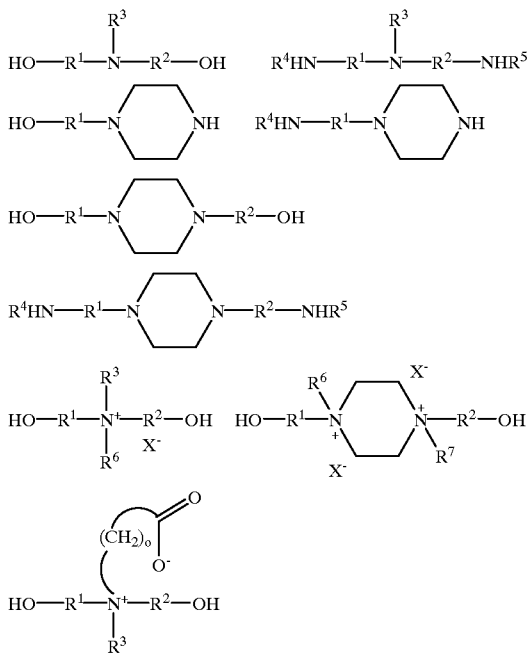

where $R^1$ and $R^2$ can be identical or different and are $C_2$–$C_8$-alkylene, $R^3$, $R^6$ and $R^7$ can be identical or different and are $C_1$–$C_6$-alkyl, phenyl or phenyl-$C_1$–$C_4$-alkyl, $R^4$ and $R^5$ can be identical or different and are H or $C_1$–$C_6$-alkyl, o is 1, 2 or 3, and $X^{\ominus}$ is chloride, bromide, iodide, $C_1$–$C_6$-alkyl sulfate or $SO_4{}^{2-}/_2$.

Component (c) comprises customary diisocyanates, especially hexamethylene diisocyanate, isophorone diisocyanate, methyldiphenyl diisocyanate (MDI) and/or tolylene diisocyanate.

Further novel polyurethane prepolymers are described in U.S. Pat. Nos. 3,475,206 and 3,412,054 and in DE-A-15 70 615, for example. Use is preferably made, however, of the polyurethanes described in DE-A-42 25 045, DE-A-42 41 118 and EP-A-619 111. The compounds involved are as follows:

1. Water-soluble or -dispersible anionic polyurethanes of
   a) at least one compound containing two or more active hydrogen atoms per molecule,
   b) at least one diol containing acid groups or salt groups, and
   c) at least one diisocyanate,
   which have a glass transition temperature of at least 15° C. and an acid number of 12–150, and the salts thereof.

Components (a), (b) and (c) are as described above.

These polymers and their preparation are described in more detail in DE-A-42 25 045, to which in its entirety reference is hereby made.

2. Water-soluble or -dispersible cationic polyurethanes and polyureas, in which context the abovementioned components (a) to (c) are used. As component (c) it is also possible to use a diisocyanate which can have already been reacted beforehand with one or more compounds containing 2 or more active hydrogen atoms per molecule, i.e. with components (a).

Such polyurethanes and their preparation are described in more detail in DE-A-42 41 118, to which in its entirety reference is hereby made.

3. Linear polyurethanes having carboxylate groups from
   a) 10–90% by weight, based on the weight of the polyurethane, of one or more organic compounds having not more than two active hydrogen atoms,
   b) a 2,2-hydroxymethyl-substituted carboxylic acid of the formula

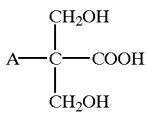

where A is hydrogen or $C_1$–$C_{20}$-alkyl, which is used in a quantity sufficient for 0.35–2.25 milliequivalents of carboxyl groups to be present per g of polyurethane, and
   c) one or more organic diisocyanates.

Components a) and c) are as indicated above.

Finally, the carboxyl groups present in the polyurethane are at least partially neutralized with an appropriate base. These polymers and their preparation are described in more detail in EP-A-619 111, to which in its entirety reference is hereby made.

The polyurethane prepolymers are obtainable by reacting the compounds of groups a) and b) with the compounds of group c) at 70–130° C. in an inert solvent or without a solvent (in the melt) under an inert gas atmosphere, and using the components in quantities such that the ratio of NCO equivalent to OH equivalent is greater than 1 and can be up to 1.2, but is preferably from 1.02 to 1.12. The acid number of the polyurethanes is determined by the composition and the concentration of the compounds of component (b) in the mixture of components (a)+(b). The polyurethanes have H. Fikentscher K values (determined in 0.1% strength by weight solutions in N-methylpyrrolidone at 25° C. and a pH of 7) of 15–100, preferably 25–50.

In accordance with a preferred embodiment, component (B) is an amine of the formula:

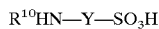

where Y is o-, m- or p-phenylene or straight-chain or branched $C_2$–$C_6$-alkylene which is unsubstituted or substituted by 1, 2 or 3 hydroxyl groups, and
   $R^{10}$ is hydrogen, $C_1$–$C_{12}$-alkyl (preferably $C_1$–$C_{10}$-alkyl and especially $C_1$–$C_6$-alkyl) or $C_5$–$C_6$-cycloalkyl, it being possible for the alkyl or cycloalkyl to be substituted, if desired, by 1, 2 or 3 hydroxyl, carboxyl or sulfo groups.

The amine of the above formula is particularly preferably taurine, N-(1,1-dimethyl-2-hydroxyethyl)-3-amino-2-hydroxypropanesulfonic acid or 4-aminobenzenesulfonic acid.

In accordance with a further preferred embodiment the amine is a customary α-, β- or γ-amino acid, for example glycine, alanine, valine, leucine, isoleucine, phenylalanine, thyrosine, proline, hydroxyproline, serine, threonine, methionine, cysteine, tryptophan or β-alanine. Preferred amino acids are aspartic acid and glutamic acid.

The novel polyurethanes are prepared by reacting the polyurethane prepolymer with the primary or secondary amine having an ionogenic or ionic group, in an appropriate inert solvent or without a solvent (in the melt). The quantity of amine used is such that the free isocyanate groups of the polyurethane prepolymer are at least partially reacted, but preferably completely reacted. Reaction is carried out in a manner known from the prior art for the termination of polyurethane polymerization with amines. Any isocyanate groups still present are subsequently deactivated by adding amines, for example 2-amino-2-methyl-1-propanol.

After replacing the solvent by water a solution or dispersion of the polymer is obtained from which the polymer can, if desired, be obtained in a customary manner, for example by spray drying.

The amine is preferably employed in the form of an aqueous or aqueous-alcoholic solution with a pH of >7.5, in order to increase the reactivity of the amine. The pH can be established in a customary manner, for example using an alkali metal hydroxide such as NaOH or KOH, or, preferably, using a tertiary amine such as triethylamine, a $C_1$–$C_6$-alkyldiethanolamine, for example methyl- or ethyldiethanolamine, or a di-$C_1$–$C_6$-alkylethanolamine.

After complete or partial neutralization, the polyurethanes containing acid groups are soluble in water or dispersible in water without the aid of emulsifiers. In general the resulting polyurethane salts are more soluble or dispersible in water than the non-neutralized polyurethanes. Suitable bases for neutralizing the polyurethanes are alkali metal bases, such as sodium hydroxide, potassium hydroxide, sodium carbonate, sodium hydrogen carbonate, potassium carbonate and potassium hydrogen carbonate, and alkaline earth metal bases, such as calcium hydroxide, calcium oxide, magnesium hydroxide and magnesium carbonate, and also ammonia and amines. Compounds which have proven particularly suitable, in the context of use in hair treatment compositions, for neutralizing the polyurethanes containing acid groups are 2-amino-2-methylpropanol, diethylaminopropylamine and triisopropanolamine. The polyurethanes containig acid groups can also be neutralized using a mixture of two or more bases, for example mixtures of sodium hydroxide solution and triisopropanolamine. Depending on the intended application, neutralization may be partial, eg. 20–40%, or complete, ie. 100%.

Where the novel compounds are dispersible in water they can be employed in the form of aqueous microdispersions with particle diameters of usually 5–100 nm, in particular 10–80 nm, and solids contents of usually 1–40% by weight, in particular 3–30% by weight. These microdispersions do not in general require any emulsifiers or surfactants in order to stabilize them.

The polyurethanes and polyureas containing free, protonated or quaternized amine groups are in general, owing to their cationic groups, readily soluble in alcohols and water, or can at least be dispersed in alcohol and water without the aid of emulsifiers. Charged cationic groups can be produced in the polyureas from the existing tertiary amine nitrogen atoms either by protonation, for example with carboxylic acids such as lactic acid, or by quaternization, for example with alkylating agents such as $C_1$–$C_4$-alkyl halides or $C_1$–$C_4$-alkyl sulfates. Examples of such alkylating agents are ethyl chloride, ethyl bromide, methyl chloride, methyl bromide, dimethyl sulfate and diethyl sulfate.

The novel polyurethanes can be used as auxiliaries in cosmetology and pharmacy, especially as coating compositions for keratin-containing surfaces (hair, skin and nails) and as coatings and/or binders for solid drug forms. They can additionally be used as coating compositions for the textile, paper, printing and adhesives industries. They are particularly suitable for use in hair cosmetology. Preferred polyurethanes employed as hair lacquers are those comprising at least 30% by weight of polyesterdiol component and having a glass transition temperature $T_g$ of $\geq 25°$ C. In addition, the polymers can also be used in creams and as coatings and binders for tablets.

The present invention additionally provides a cosmetic or pharmaceutical composition comprising the novel polyurethanes, generally in a quantity of 0.2–20% of the overall weight of the composition.

Preference is given to hair treatment compositions. These are usually in the form of an aqueous dispersion or an alcoholic or aqueous-alcoholic solution. Examples of appropriate alcohols are ethanol, propanol, isopropanol, etc.

Furthermore, the novel hair treatment compositions generally comprise customary cosmetic auxiliaries, examples being softeners, such as glycerol and glycol; emollients; fragrances; UV absorbers; colorants; thickeners; antistats; combability improvers; preservatives; and foam stabilizers.

When formulated as hairsprays, the novel compositions comprise a sufficient quantity of a propellent, for example a low-boiling hydrocarbon or ether, such as propane, butane, isobutane or dimethyl ether. As propellents it is also possible to use compressed gases, such as nitrogen, air or carbon dioxide. The amount of propellent is kept as low as possible so as not unnecessarily to raise the VOC content. In general it is not more than 40% of the overall weight of the composition.

The polyurethanes of the invention can also be employed in the compositions in combination with other hair polymers. Such polymers are, in particular:

nonionic, water-soluble or water-dispersible polymers or oligomers, such as polyvinylcaprolactam, eg. Luviskol Plus (BASF), or polyvinylpyrrolidone and its copolymers, especially with vinyl esters such as vinyl acetate, eg. Luviskol VA 37 (BASF); polyamides, for example those based on itaconic acid and aliphatic diamines amphoteric or zwitterionic polymers, such as the octylacrylamide/methyl methacrylate/tert-butylaminoethyl methacrylate/2-hydroxypropyl methacrylate copolymers obtainable under the designations Amphomer® (Delft National), and zwitterionic polymers as disclosed, for example, in German Patent Applications DE 39 29 973, DE 21 50 557, DE 28 17 369 and DE 37 08 451. Acrylamidopropyltrimethylammonium chloride/acrylic acid and/or methacrylic acid copolymers, and the alkali metal salts and ammonium salts thereof, are preferred zwitterionic polymers. Suitable zwitterionic polymers are also methacroylethyl betaine/methacrylate copolymers, which are obtainable commercially under the designation Amersette® (AMERCHOL).

water-soluble or water-dispersible polymers with the same ionogenicity as the polymers of the invention, ie. anionic polyurethanes of the invention and anionic polymers, such as vinyl acetate/crotonic acid copolymers, as are in commerce, for example, under the designations Resyn® (NATIONAL STARCH), Luviset® (BASF) and Gafset® (GAF), vinylpyrrolidone/vinyl acrylate copolymers, obtainable for example under the trademark Luviflex® (BASF). A preferred polymer is the vinylpyrrolidone/acrylate terpolymer obtainable under the designation Luviflex® VBM-35 (BASF), acrylic acid/ethyl acrylate/N-tert-butylacrylamide terpolymers, which are marketed, for example, under the designation Ultrahold® strong (BASF), and Luvimer® (BASF, terpolymer of t-butyl acrylate, ethyl acrylate and methacrylic acid), or cationic polyurethanes of the invention and cationic (quaternized) polymers, eg. Luviquat® (copolymer of vinylpyrrolidone and vinylimidazolium methochloride), Luviquat® Hold (copolymer of quaternized N-vinylimidazole, N-vinylpyrrolidone and N-vinylcaprolactam), Merquat® (polymer based on dimethyldiallylammonium chloride) Gafquat® (quaternary polymers formed by reacting polyvinylpyrrolidone with quaternary ammonium compounds), Polymer JR (hydroxyethylcellulose with cationic groups), polyquaternium types (CTFA names), etc.

neutral, siloxane-containing, water-soluble or -dispersible polymers, eg. polyethersiloxanes, such as Tegopren® (Goldschmidt).

The other hair polymers are preferably present in amounts of up to 10% by weight, based on the overall weight of the composition. A particularly preferred hair treatment composition comprises:

a) at least one siloxane-free, water-soluble or -dispersible hair polymer, especially hairsetting polymer, which can be either a polyurethane of the invention or another hair polymer, b) at least one polysiloxane-containing polyurethane as defined above and c) a water-insoluble non-volatile silicone, especially a polydimethylsiloxane, eg. the Abil grades from Goldschmidt.

The composition preferably contains 0.1–10% by weight of component a), 0.1–15% by weight of component b) and from 0.0001 to 0.2% by weight of component c).

The novel polyurethanes and compositions have the advantage that firstly they give the hair the desired set and secondly the polymers are easier to wash off (more redispersible) than their prior art counterparts. Furthermore, it is possible to formulate hair treatment compositions with a VOC content of less than 60% by weight and also to prepare purely aqueous formulations, even if they are formulated as hairsprays.

The examples which follow illustrate the invention.

EXAMPLE 1

Polyurethane preparation:

0.5 mol of polyesterdiol ($M_w$=1,000 g/mol, prepared from isophthalic acid, adipic acid and hexanediol), 0.6 mol of diethylene glycol and 1.25 mol of dimethylolpropanoic acid in methyl ethyl ketone (about 50% strength) were heated to 80° C. with stirring to form a solution in a 4-necked flask fitted with stirrer, dropping funnel, thermometer, reflux condenser and a device for working under nitrogen. Immediately after complete dissolution, the reaction mixture was cooled to about 50° C. Then 2.5 mol of isophorone diisocyanate were added dropwise, while stirring, and the reaction temperature rose. At an internal temperature of 90° C., the reaction mixture was then stirred until its content of isocyanate groups remained virtually constant. It was then cooled to ambient temperature, at which 0.3 mol of (a) aspartic acid or (b) glutamic acid or (c) taurine was added, in each case in the form of a 50% strength aqueous solution of amino acid and diethylethanol-amine, the latter being used in a quantity equimolar with the amino acid. The reaction mixture was then stirred at ambient temperature until its content of isocyanate groups was 0. Water was then added and the reaction product was neutralized with 2-amino-2-methylpropanol. The methyl ethyl ketone was then distilled off under reduced pressure at 40° C. to give an aqueous polyurethane dispersion which was used for the tests described in Examples 3 and 4 below.

EXAMPLE 2

Polyurethane preparation (without adding an amino acid)

0.5 mol of polyesterdiol ($M_w$=1,000 g/mol, prepared from isophthalic acid, adipic acid and hexanediol), 0.5 mol of diethylene glycol and 1.25 mol of dimethylolpropanoic acid in methyl ethyl ketone (about 50% strength) were heated to 80° C. with stirring to form a solution in a 4-necked flask fitted with stirrer, dropping funnel, thermometer, reflux condenser and a device for working under nitrogen. Immediately after complete dissolution, the reaction mixture was cooled to about 50° C. Then 2.5 mol of isophorone diisocyanate were added dropwise, while stirring, and the reaction temperature rose. At a reflux temperature, the reaction mixture was then stirred until its content of isocyanate groups remained virtually constant. The residual isocyanate groups were deactivated by adding an amine, for example 2-amino-2-methyl-1-propanol. Free COOH groups were neutralized with 2-amino-2-methylpropanol. Water was then added and the largest part of the methyl ethyl ketone was removed under reduced pressure at about 40° C. to give a polyurethane dispersion which was used for comparison for the tests described in Example 4 below.

EXAMPLE 3

Determination of the ease of washoff of the polymers:

The ease of washoff with water of the polymers obtained as described in Example 1 was compared with that of a polymer in which the terminal isocyanate groups have been reacted not with an amino acid but with 2-amino-2-methylpropanol. For this purpose, a film obtained from a 5% strength aqueous dispersion and a film obtained from an aqueous ethanolic dispersion (1:1 v/v) of the polymer were produced on a glass plate by pouring the individual polymer dispersion onto the glass plate and then drying it at room temperature for 20 h. The ease of washoff (redispersibility) of the film prepared from water or water/ethanol (1:1 v/v) was determined by rubbing with the finger. The results obtained are indicated in the table below.

TABLE

Ease of washoff of the polymers

| Test | K value of the polyurethane | Amino acid | Ease of washoff Film from aqueous dispersion | Ease of washoff Film from $H_2O$/EtOH dispersion |
|---|---|---|---|---|
| 1 | 27 | — | poor | poor |
| 2 | 27 | Asp | good | good |
| 3 | 27 | Glu | good | good |
| 4 | 27 | Tau | good | good |

Asp = aspartic acid
Glu = glutamic acid
Tau = taurine

It is evident that, surprisingly, the films obtained with the novel compositions are easier to wash off than the film obtained with the prior art composition.

EXAMPLE 4

| Hairspray formulation with a VOC content of 55% by weight: | |
|---|---|
| Polyurethane of Example 1 (solids content) | 5.00% by wt. |
| Water | 40.00% by wt. |
| Ethanol | 25% by wt. |
| Dimethyl ether | 30% by wt. |
| Fragrance | q.s. |

The ease of washoff of the film obtained with this formulation was compared with that of a film obtained with the same formulation but containing the polyurethane as described in Example 2. The ease of washoff was determined as follows:

The hairspray was applied in a 10-second spray procedure (quantity applied about 2.5 g) to the hair of synthetic headforms. After drying for two hours in a climate-controlled room (atmospheric humidity 45%; temperature 20° C.), the setting effect was assessed. This procedure was repeated a total of 3 times. The sprayed headform was dried overnight in the climate-controlled room and then shampooed with Texapon NSO for minutes or less and washed. After drying, the ease of washoff was assessed by trained technical staff. It was found that the film obtained with the novel formulation was easy to wash off, whereas washoff of the film obtained with the polyurethane as described in Example 2 was difficult.

We claim:
1. A water-soluble or water-dispersible polyurethane or a salt thereof comprising

A) a water-soluble or -dispersible polyurethane prepolymer having terminal isocyanate groups formed from
a) at least one compound containing two or more active hydrogen atoms per molecule selected from diols, diamines, aminoalcohols, polyetherdiols, polyesterdiols each with a number average molecular weight of up to 3000, or mixtures thereof, wherein if the at least one compound of component a) comprises a polyesterdiol then the polyesterdiol is the reaction product of an aromatic dicarboxylic acid and an aliphatic dicarboxylic acid and an aliphatic diol,
b) at least one compound different from the at least one compound of component a), containing two or more active hydrogen atoms and at least one ionogenic or ionic group per molecule which is a carboxylate group or nitrogen-containing group, wherein if the at least one compound of component b) contains a nitrogen-containing group, then the at least one compound of component b) is selected from the group consisting of

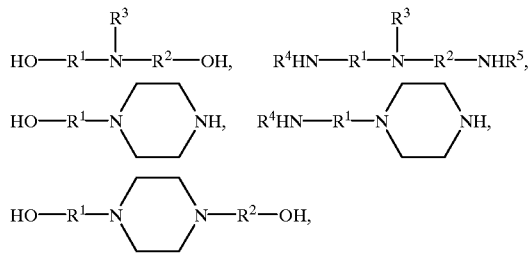

-continued

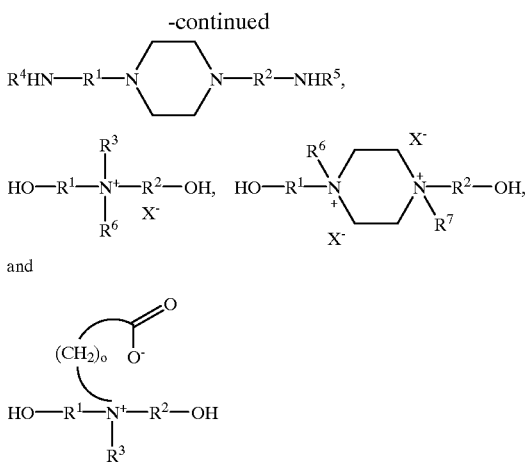

and

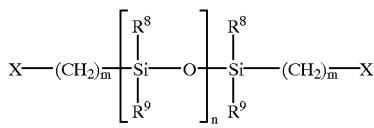

where
- $R^1$ and $R^2$ are identical or different and are $C_2$–$C_8$-alkylene,
- $R^3$, $R^6$ and $R^7$ are identical or different and are $C_1$–$C_6$-alkyl, phenyl or phenyl-$C_1$–$C_4$-alkyl,
- $R^4$ and $R^5$ are identical or different and are H or $C_1$–$C_6$-alkyl,
- o is 1, 2 or 3, and
- $X^-$ is chloride, bromide, iodide, $C_1$–$C_6$-alkyl sulfate or $SO_4^{2-}/2$, and
  c) at least one diisocyanate selected from isophorone diisocyanate, methylenediphenyl diisoscyanate or toluylene diisocyanate, and
B) at least one primary or secondary amine having at least one ionogenic or ionic group;
wherein component a) comprises an amount up to 50% by weight, based on the overall weight of components a) and b), of a silicone compound of the formula $$X-(CH_2)_{\overline{m}}\left[\begin{array}{c}R^8\\|\\Si\\|\\R^9\end{array}-O\right]\left[\begin{array}{c}R^8\\|\\Si\\|\\R^9\end{array}\right]_n(CH_2)_{\overline{m}}-X$$

where $R^8$ and $R^9$ are identical or different and are $C_1$–$C_4$-alkyl, benzyl or phenyl, the radicals X are identical or different and are OH or $NH_2$,
m is 2–8, and
n is 3–50.

2. A polyurethane as claimed in claim 1, where component (a) is a polyesterdiol which is the reaction product of an aromatic dicarboxylic acid and an aliphatic dicarboxylic acid and an aliphatic diol.

3. A polyurethane as claimed in claim 2, where the proportion of the aromatic dicarboxylic acid makes up from 10 to 95 mol-% of the overall dicarboxylic acid.

4. A polyurethane as claimed in claim 2, where the proportion of the aromatic dicarboxylic acid makes up from 40 to 90 mol-% of the overall dicarboxylic acid.

5. A polyurethane as claimed in claim 2, where the proportion of the aromatic dicarboxylic acid makes up from 50 to 85 mol-% of the overall dicarboxylic acid.

6. A polyurethane as claimed in claim 1, wherein component a) comprises 40 to 80 % by weight, based on the overall weight of components a) and b), of a polyesterdiol.

7. A polyurethane as claimed in claim 1, wherein up to 3 mol-% of the at least one compound of component a) is replaced by triols or triamines.

8. A polyurethane as claimed in claim 1, wherein the ratio of NCO equivalent of the compounds of group c) to equivalent of active hydrogen atom of the compounds of group a) and b) is from greater than 1:1 to 1.2:1.

9. A polyurethane as claimed in claim 1, wherein component b) is dimethylolpropanoic acid.

10. A polyurethane as claimed in claim 1, wherein component a) comprises at least 30% by weight based on the overall weight of components a) and b), of a polyesterdiol.

11. A polyurethane as claimed in claim 1, wherein component (B) is an aminosulfonic acid of the formula $$R^{10}HN-Y-SO_3H$$

where Y is o-, m- or p-phenylene or straight-chain or branched $C_2$–$C_6$-alkylene which is unsubstituted or substituted by 1, 2 or 3 hydroxyl groups, and
$R^{10}$ is hydrogen, $C_1$–$C_{12}$-alkyl or $C_5$–$C_6$-cycloalkyl, wherein the alkyl or cycloalkyl are optionally substituted by 1, 2 or 3 hydroxyl, carboxyl or sulfo groups.

12. A polyurethane as claimed in claim 11, wherein the amine is taurine, N-(1,1-dimethyl-2-hydroxyethyl)-3-amino-2-hydroxy-propanesulfonic acid or 4-aminobenzenesulfonic acid.

13. A process for preparing a polyurethane as claimed in claim 1, which comprises reacting the polyurethane prepolymer with a primary or secondary amine.

14. A water-soluble or water-dispersible polyurethane or a salt thereof comprising
A) a water-soluble or -dispersible polyurethane prepolymer having terminal isocyanate groups formed from
  a) at least one compound containing two or more active hydrogen atoms per molecule selected from diols, diamines, aminoalcohols, polyetherdiols, polyesterdiols each with a number average molecular weight of up to 3000, or mixtures thereof, wherein if the at least one compound of component a) comprises a polyesterdiol then the polyesterdiol is the reaction product of an aromatic dicarboxylic acid and an aliphatic dicarboxylic acid and an aliphatic diol,
  b) at least one compound different from the at least one compound of component a), containing two or more active hydrogen atoms and at least one ionogenic or ionic group per molecule which is a carboxylate group or nitrogen-containing group,
wherein if the at least one compound of component b) contains a nitrogen-containing group, then the at least one compound of component b) is selected from the group consisting of

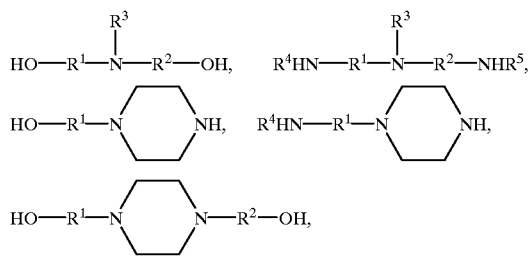

-continued

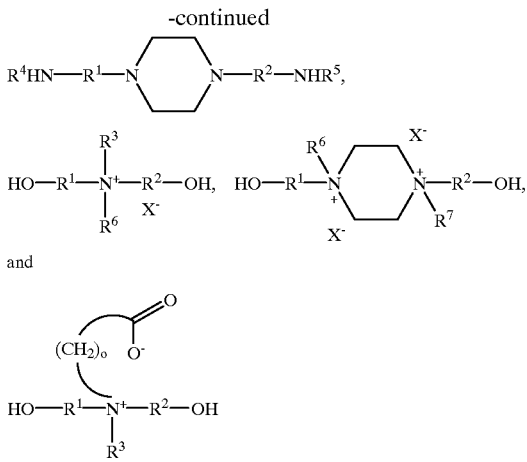

where
- $R^1$ and $R^2$ are identical or different and are $C_2$–$C_8$-alkylene,
- $R^3$, $R^6$ and $R^7$ are identical or different and are $C_1$–$C_6$-alkyl, phenyl or phenyl-$C_1$–$C_4$-alkyl,
- $R^4$ and $R^5$ are identical or different and are H or $C_1$–$C_6$-alkyl,
- o is 1, 2 or 3, and
- $X^-$ is chloride, bromide, iodide, $C_1$–$C_6$-alkyl sulfate or $SO_4^{2-}/2$, and
  c) at least one diisocyanate selected from isophorone diisocyanate, methylenediphenyl diisoscyanate or toluylene diisocyanate, and
B) at least one primary or secondary amine having at least one ionogenic or ionic group,
wherein component (B) is an α-, β- or γ-aminocarboxylic acid.

15. A polyurethane as claimed in claim 14, wherein the amino acid is aspartic acid or glutamic acid.

16. A cosmetic or pharmaceutical composition comprising at least one water-soluble or water-dispersible polyurethane or a salt thereof comprising
   A) a water-soluble or -dispersible polyurethane prepolymer having terminal isocyanate groups formed from
     a) at least one compound containing two or more active hydrogen atoms per molecule selected from diols, diamines, aminoalcohols, polyetherdiols, polyesterdiols each with a number average molecular weight of up to 3000, or mixtures thereof,
     b) at least one compound different from the at least one compound of component a), containing two or more active hydrogen atoms and at least one ionogenic or ionic group per molecule which is a carboxylate group or nitrogen-containing group,
wherein if the at least one compound of component b) contains a nitrogen-containing group, then the at least one compound of component b) is selected from the group consisting of

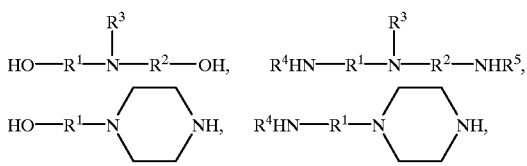

-continued

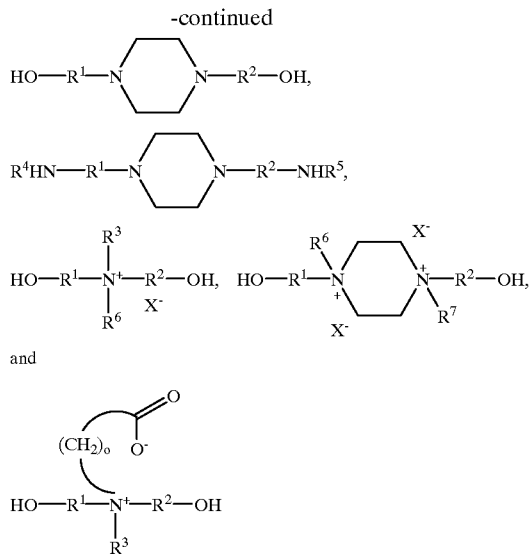

where
- $R^1$ and $R^2$ are identical or different and are $C_2$–$C_8$-alkylene,
- $R^3$, $R^6$ and $R^7$ are identical or different and are $C_1$–$C_6$-alkyl, phenyl or phenyl-$C_1$–$C_4$-alkyl,
- $R^4$ and $R^5$ are identical or different and are H or $C_1$–$C_6$-alkyl,
- o is 1, 2 or 3, and
- $X^-$ is chloride, bromide, iodide, $C_1$–$C_6$-alkyl sulfate or $SO_4^{2-}/2$, and
  c) at least one diisocyanate selected from isophorone diisocyanate, methylenediphenyl diisoscyanate or toluylene diisocyanate, and
B) at least one primary or secondary amine having at least one ionogenic or ionic group.

17. A composition as claimed in claim 16, wherein component a) comprises up to 50% by weight, based on the overall weight of components a) and b), of a silicone compound of the formula

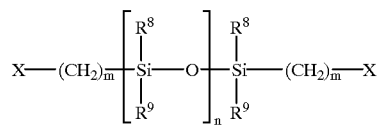

where $R^8$ and $R^9$ are identical or different and are $C_1$–$C_4$-alkyl, benzyl or phenyl, the radicals X are identical or different and are OH or $NH_2$,
m is 2–8, and
n is 3–50,
said composition further comprising at least one water-insoluble silicone.

18. A composition as claimed in claim 17, wherein the water-insoluble silicone is polydimethylsiloxane.

19. A composition as claimed in claim 17, further comprising at least one siloxane-free, water soluble or -dispersible hair polymer.

20. A composition as claimed in claim 19, wherein the water-insoluble silicone is polydimethylsiloxane.

21. A hair treatment composition comprising at least one water-soluble or water-dispersible polyurethane or a salt thereof comprising A) a water-soluble or -dispersible polyurethane prepolymer having terminal isocyanate groups formed from
  a) at least one compound containing two or more active hydrogen atoms per molecule selected from diols, diamines, aminoalcohols, polyetherdiols, polyesterdiols each with a number average molecular weight of up to 3000, or mixtures thereof,
  b) at least one compound different from the at least one compound of component a), containing two or more active hydrogen atoms and at least one ionogenic or ionic group per molecule which is a carboxylate group or nitrogen-containing group,
wherein if the at least one compound of component b) contains a nitrogen-containing group, then the at least one compound of component b) is selected from the group consisting of

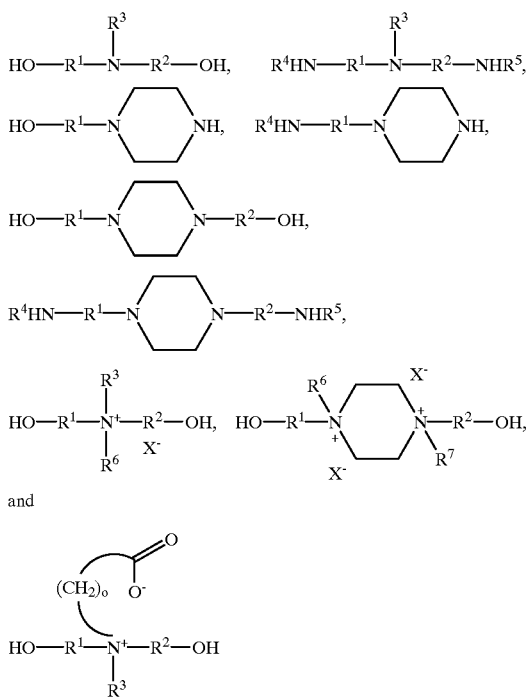

where
  $R^1$ and $R^2$ are identical or different and are $C_2$–$C_8$-alkylene,
  $R^3$, $R^6$ and $R^7$ are identical or different and are $C_1$–$C_6$-alkyl, phenyl or phenyl-$C_1$–$C_4$-alkyl,
  $R^4$ and $R^5$ are identical or different and are H or $C_1$–$C_6$-alkyl,
  o is 1, 2 or 3, and
  $X^-$ is chloride, bromide, iodide, $C_1$–$C_6$-alkyl sulfate or $SO_4^{2-}/2$, and
  c) at least one diisocyanate selected from isophorone diisocyanate, methylenediphenyl diisoscyanate or toluylene diisocyanate, and
B) at least one primary or secondary amine having at least one ionogenic or ionic group.

22. A composition as claimed in claim 21, which additionally comprises at least one other water-soluble or -dispersible hair polymer.

23. A hairspray comprising at least one water-soluble or water-dispersible polyurethane or a salt thereof comprising
A) a water-soluble or -dispersible polyurethane prepolymer having terminal isocyanate groups formed from
  a) at least one compound containing two or more active hydrogen atoms per molecule selected from diols, diamines, aminoalcohols, polyetherdiols, polyesterdiols each with a number average molecular weight of up to 3000, or mixtures thereof, wherein if the at least one compound of component a) comprises a polyesterdiol then the polyesterdiol is the reaction product of an aromatic dicarboxylic acid and an aliphatic dicarboxylic acid and an aliphatic diol,
  b) at least one compound different from the at least one compound of component a), containing two or more active hydrogen atoms and at least one ionogenic or ionic group per molecule which is a carboxylate group or nitrogen-containing group,
wherein if the at least one compound of component b) contains a nitrogen-containing group, then the at least one compound of component b) is selected from the group consisting of

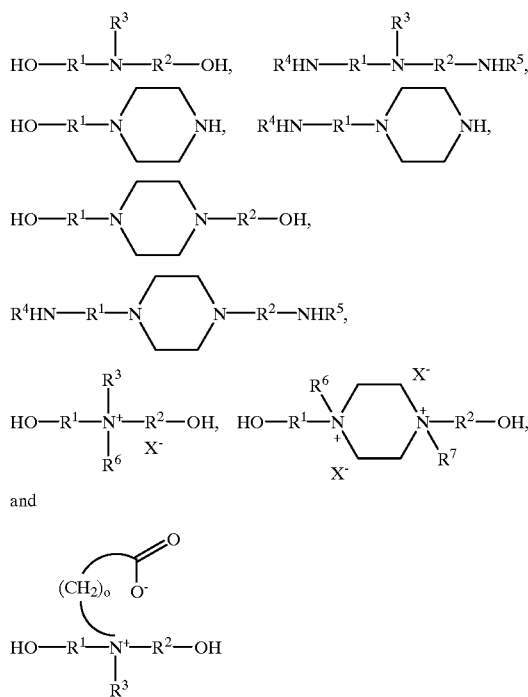

where
  $R^1$ and $R^2$ are identical or different and are $C_2$–$C_8$-alkylene,
  $R^3$, $R^6$ and $R^7$ are identical or different and are $C_1$–$C_6$-alkyl, phenyl or phenyl-$C_1$–$C_4$-alkyl,
  $R^4$ and $R^5$ are identical or different and are H or $C_1$–$C_6$-alkyl,
  o is 1, 2 or 3, and
  $X^-$ is chloride, bromide, iodide, $C_1$–$C_6$-alkyl sulfate or $SO_4^{2-}/2$, and
  c) at least one diisocyanate selected from isophorone diisocyanate, methylenediphenyl diisoscyanate or toluylene diisocyanate, and
B) at least one primary or secondary amine having at least one ionogenic or ionic group.

* * * * *

UNITED STATES PATENT AND TRADEMARK OFFICE
CERTIFICATE OF CORRECTION

PATENT NO.    : 6,365,697 B1
DATED         : April 2, 2002
INVENTOR(S)   : Kim et al.

It is certified that error appears in the above-identified patent and that said Letters Patent is hereby corrected as shown below:

<u>Title page,</u>
Item [22], "Nov. 6, 1995" should be -- Nov. 6, 1996 --.

Signed and Sealed this

Twenty-ninth Day of July, 2003

JAMES E. ROGAN
*Director of the United States Patent and Trademark Office*